(12) United States Patent
Li

(10) Patent No.: US 11,026,819 B2
(45) Date of Patent: Jun. 8, 2021

(54) VASCULAR STENT, CONVEYING BALLOON THEREOF, AND IMPLANTING SYSTEM

(71) Applicant: Lei Li, Beijing (CN)

(72) Inventor: Lei Li, Beijing (CN)

(73) Assignee: Evans Scientific (Beijing) Co., Ltd, Beijing (CN)

( * ) Notice: Subject to any disclaimer, the term of this patent is extended or adjusted under 35 U.S.C. 154(b) by 246 days.

(21) Appl. No.: 16/064,821

(22) PCT Filed: Oct. 19, 2016

(86) PCT No.: PCT/CN2016/102621
§ 371 (c)(1),
(2) Date: Nov. 27, 2018

(87) PCT Pub. No.: WO2017/107633
PCT Pub. Date: Jun. 29, 2017

(65) Prior Publication Data
US 2019/0083288 A1   Mar. 21, 2019

(30) Foreign Application Priority Data
Dec. 25, 2015 (CN) .......................... 201510997585.3

(51) Int. Cl.
*A61F 2/945* (2013.01)
*A61F 2/958* (2013.01)
(Continued)

(52) U.S. Cl.
CPC ................. *A61F 2/945* (2013.01); *A61F 2/82* (2013.01); *A61F 2/88* (2013.01); *A61F 2/95* (2013.01);
(Continued)

(58) Field of Classification Search
CPC ...... A61F 2250/0003; A61F 2210/0085; A61F 2/07; A61F 2/945; A61F 2/95;
(Continued)

(56) References Cited

U.S. PATENT DOCUMENTS 5,980,570 A   11/1999  Simpson
6,059,823 A    5/2000  Holman et al.
(Continued)

FOREIGN PATENT DOCUMENTS

CA   2205192 A   11/1997
CN   1715312 A    1/2006
(Continued)

OTHER PUBLICATIONS

International Search Report and English translation for PCT/CN2016/102621 dated Jan. 20, 2017.
(Continued)

*Primary Examiner* — Katherine M Shi
(74) *Attorney, Agent, or Firm* — Caesar Rivise, PC

(57) ABSTRACT

Provided are a vascular stent, a conveying balloon thereof, and an implanting system. The vascular stent comprises a flexible light-transmitting body. The flexible light-transmitting body is provided with a hardenable channel. The hardenable channel is arranged in the circumferential direction and the axial direction of the flexible light-transmitting body. The hardenable channel is used for filling a liquid photocuring supporting material, and the liquid photocuring supporting material is cured after being illuminated so as to radially support the flexible light-transmitting body.

6 Claims, 3 Drawing Sheets

(51) Int. Cl.
  *A61F 2/88* (2006.01)
  *A61F 2/82* (2013.01)
  *A61F 2/95* (2013.01)
(52) U.S. Cl.
  CPC ...... *A61F 2/958* (2013.01); *A61F 2210/0085* (2013.01); *A61F 2250/0091* (2013.01)
(58) Field of Classification Search
  CPC .... A61F 2/954; A61F 2/958; A61F 2002/072; A61F 2002/30583; A61F 2/2427; A61F 2/82; A61F 2/88; A61F 2/94; A61B 17/12118; A61B 2017/1205; Y10S 623/903
  See application file for complete search history.

(56) References Cited

U.S. PATENT DOCUMENTS

| | | |
|---|---|---|
| 2007/0282424 A1 | 12/2007 | Holman et al. |
| 2008/0215138 A1* | 9/2008 | Bates ................ A61L 31/10 623/1.42 |
| 2014/0364866 A1 | 12/2014 | Dryden et al. |

FOREIGN PATENT DOCUMENTS

| | | |
|---|---|---|
| EP | 0808613 A1 | 11/1997 |
| EP | 2 005 917 A1 | 12/2008 |
| EP | WO 03/057075 A3 | 12/2008 |
| JP | 2008-541936 A | 11/2008 |
| JP | 2009-276 A | 1/2009 |
| WO | WO 03/057075 A2 | 7/2003 |

OTHER PUBLICATIONS

Communication from the European Patent Office in counterpart European Application No. 16877444.6, dated Dec. 21, 2018.
Communication from the Japanese Patent Office in counterpart application No. 2018-533735, dated May 7, 2019.
Communication from the Japanese Patent Office in counterpart application No. 2018-533735, dated Oct. 13, 2020.

* cited by examiner

VASCULAR STENT, CONVEYING BALLOON THEREOF, AND IMPLANTING SYSTEM

CROSS REFERENCE

This application is the U.S. national phase entry of PCT/CN2016/102621 with an international filing date of 19 Oct. 2016, which claims the benefit of Chinese Patent Application No. 201510997585.3 with a filing date of 25 Dec. 2015, the entire disclosures of which are fully incorporated herein by reference.

TECHNICAL FIELD

The present invention relates to the field of interventional therapy medical instruments, and more particularly relates to a vascular stent, a conveying balloon thereof, and an implanting system.

BACKGROUND ART

The interventional therapy of a vascular stent is widely used in the therapy of cardiovascular and cerebrovascular diseases such as vascular occlusion. For example, it is often necessary to implant a covered stent in great blood vessels such as aorta and metal stents in other small blood vessels. The metal stent realizes radial support through its own structure, and the covered stent includes a metal stent having a radial supporting effect and a flexible membrana tectoria fitted to the outside of the metal stent, so that the flexible membrana tectoria is tightly attached to a vessel wall by the supporting force of the metal stent. The cost of the metal stent is relatively high, the cost of the existing covered stent is also high accordingly, and it is inconvenient to implant.

SUMMARY OF THE INVENTION

The present invention is directed to a vascular stent, a conveying balloon for conveying the vascular stent, and an implanting system for implanting the vascular stent. The vascular stent has a simple structure, has an effective radial supporting effect in the absence of a metal stent, is convenient to implant and has lower cost.

To this end, according to an aspect of the present invention, a vascular stent is provided. The vascular stent includes a flexible light-transmitting body. The flexible light-transmitting body is provided with a hardenable channel. The hardenable channel is arranged in the circumferential direction and the axial direction of the flexible light-transmitting body. The hardenable channel is used for filling a liquid photocuring supporting material, and the liquid photocuring supporting material is cured after being illuminated so as to radially support the flexible light-transmitting body.

Preferably, the liquid photocuring supporting material is UV resin.

Preferably, the hardenable channel is a spiral tubular structure extending along a side wall of the flexible light-transmitting body.

Preferably, the hardenable channel is a mesh structure arranged along a side wall of the flexible light-transmitting body.

Preferably, the vascular stent is an aortic vascular stent.

Preferably, the flexible light-transmitting body is made of a polyvinylidene fluoride material.

According to another aspect of the present invention, a conveying balloon for a vascular stent provided in the present invention is provided. The conveying balloon includes a balloon body and a control pipeline for filling the balloon body with air or liquid. A light source is disposed in the balloon body, and a side wall of the balloon body is made of a light-transmitting material.

According to yet another aspect of the present invention, an implanting system for a vascular stent is provided. The implanting system includes a stent conveying device for releasably receiving a vascular stent. The vascular stent is a vascular stent provided in the present invention. The implanting system includes a light source for illuminating the vascular stent, and a liquid supply pipe for conveying a liquid photocuring supporting material. The liquid supply pipe is detachably connected to the vascular stent.

Preferably, the stent conveying device is a conveying balloon. The conveying balloon includes a balloon body and a control pipeline for filling the balloon body with air or liquid. A light source is disposed in the balloon body, and a side wall of the balloon body is made of a light-transmitting material.

Preferably, the implanting system further includes a pipe cutting assembly. The pipe cutting assembly includes a top core and a cutting wire. A distal end surface of the top core is formed with a cutting groove. Two ends of the cutting wire movably penetrate through the top core along the axial direction from the cutting groove and stretch out from a proximal end, and the liquid supply pipe passes between the cutting wire and the cutting groove.

By means of the above technical schemes, the present invention innovatively adopts the characteristic that the liquid photocuring material is hardened into a fixed material after being illuminated, to radially support the flexible light-transmitting body; by means of the hardenable channel extending in the circumferential direction and the axial direction, it can be ensured that the implanted vascular stent has a good radial supporting capability; and the vascular stent provided in the present invention has a simple structure, is convenient to implant and has lower cost compared with a metal stent.

Additional features and advantages of the present invention will be set forth in part in the following detailed description of the invention.

BRIEF DESCRIPTION OF THE DRAWINGS

Drawings are used to provide further understandings of the present invention, and constitute a part of the description. The drawings and the following detailed description of the invention serve to explain the present invention and do not constitute a limitation to the present invention. In drawings.

DRAWING REFERENCE SIGNS

Figure 1:
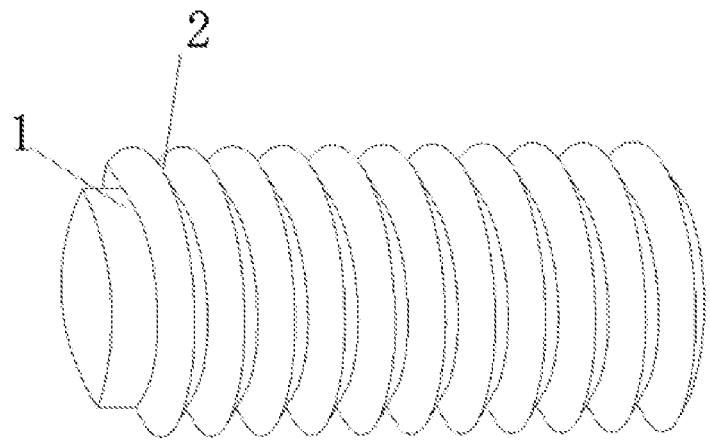
FIG. 1 is a structure schematic diagram of a vascular stent provided by an implementation of the present invention.

1 Flexible light-transmitting body 2 Hardenable channel
3 Liquid photocuring supporting material 4 Balloon body
5 Light source 6 Light beam
7 Light-emitting diode LED 8 Liquid supply pipe
91 Cutting groove 92 Top core
93 Cutting wire 94 Guide hole

DETAILED DESCRIPTION OF THE INVENTION

Specific implementations of the present invention will be described with reference to the drawings in detail below. It will be appreciated that the specific implementations described herein are only used to illustrate and explain the present invention and are not intended to limit the present invention.

In the present invention, prepositions such as "far and near" are defined on the basis of a human intervention point when a vascular stent implanting therapy is performed, unless otherwise specified. That is, a direction far from the intervention point is far, and a direction close to the intervention point is near. In addition, prepositions "inside and outside" are defined with the inside and outside of the contour of a corresponding object.

Figure 2:
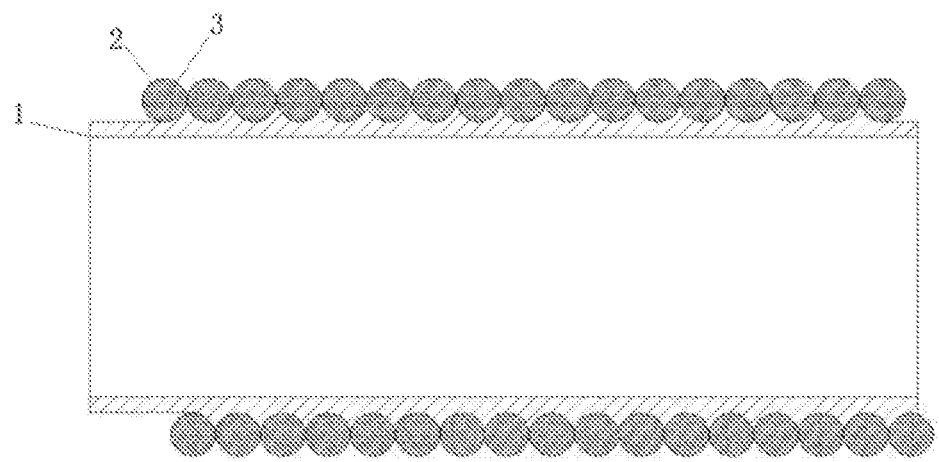
FIG. 2 is a sectional structure schematic diagram of a vascular stent in FIG. 1.

As shown in FIG. 1 and FIG. 2, the present invention provides a vascular stent, a conveying balloon thereof, and an implanting system. The vascular stent includes a flexible light-transmitting body 1. The flexible light-transmitting body 1 is provided with a hardenable channel 2. The hardenable channel 2 is arranged in the circumferential direction and the axial direction of the flexible light-transmitting body 1. The hardenable channel 2 fills a liquid photocuring supporting material 3, and the liquid photocuring supporting material 3 is characterized by being cured after being illuminated so as to radially support the flexible light-transmitting body 1. In this way, during the implantation of the vascular stent, the flexible light-transmitting body may be compressed to complete conveying, and when the vascular stent is conveyed to a designated position, the flexible light-transmitting body 1 may be expanded and fitted to an inner wall of a blood vessel by conveying the liquid photocuring supporting material into the flexible light-transmitting body 1. Then, the liquid photocuring supporting material 3 is cured by light passing through the flexible light-transmitting body 1, so as to achieve a radial supporting effect on the blood vessel.

The application field of the vascular stent may be similar to that of a covered stent. Particularly, the vascular stent may be used as an aortic vascular stent. The flexible light-transmitting body 1 may be made of the same material as that of the existing covered stent, such as polyvinylidene fluoride (PVDF). In addition, the flexible light-transmitting body 1 having flexibility and light transmission may also be made of polytetrafluoroethylene PDFE. In addition, the vascular stent provided in the present invention is similar to the application field of the covered stent, and may also be applied to the field of common metal stents, thereby effectively improving the cost and efficiency of interventional therapy.

In this way, the present invention innovatively adopts the photocuring material to radially support the flexible light-transmitting body; by means of the hardenable channel extending in the circumferential direction and the axial direction, it can be ensured that the implanted vascular stent has a good radial supporting capability; and the vascular stent provided in the present invention has a simple structure, is convenient to implant and has lower cost. In the implementation of the present invention, the liquid photocuring supporting material 3 capable of having the above characteristics is a photocuring material that can be cured after being illuminated, such as UV resin, to achieve the purpose of the present invention.

In addition, in order to provide a good radial supporting force, as shown in FIG. 1, as an embodiment, the hardenable channel 2 may be a spiral tubular structure extending along a side wall of the flexible light-transmitting body 1. The spiral structure can well axially and circumferentially extend and can provide a good radial supporting force. In other embodiments, the hardenable channel 2 is a mesh structure arranged along the sidewall of the flexible light-transmitting body 1 and can also provide a good radial supporting force, wherein the mesh structure may be formed by alternately connecting more than two bolt tubular structures or formed by connecting multiple annular pipes and axial pipes. In addition, in order to facilitate the addition of the liquid photocuring supporting material 3, various parts of the mesh structure communicate with each other, so that the liquid photocuring supporting material 3 may be easily injected into the mesh structure through an addition port.

Figure 3:
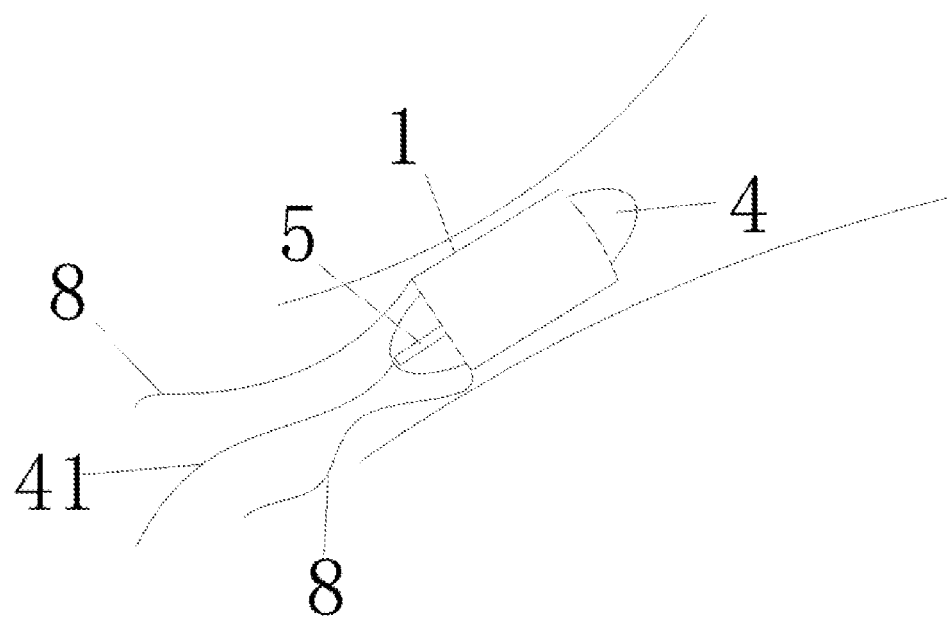
FIG. 3 is a structure schematic diagram of an implanting system provided by an implementation of the present invention.
Figure 4:
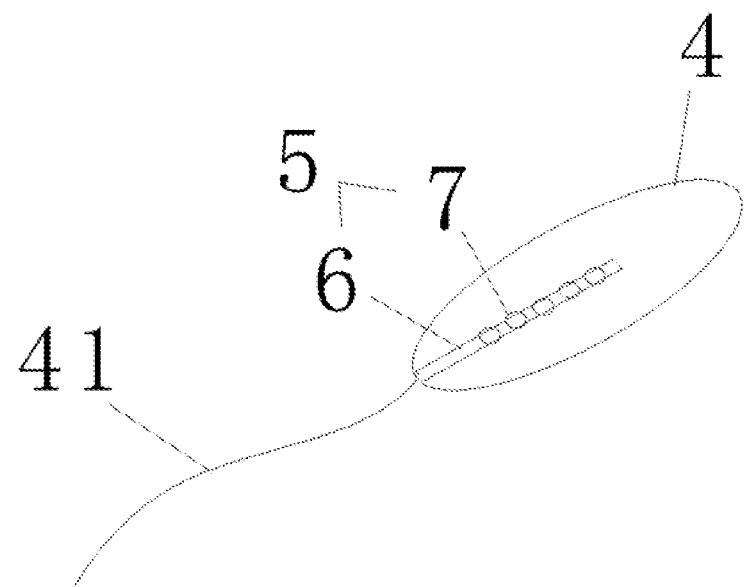
FIG. 4 is a structure schematic diagram of a conveying balloon provided by an implementation of the present invention.

In addition, the implantation of the vascular stent is completed, that is, the photocuring process after positioning the flexible light-transmitting body is implemented. The present invention provides a conveying balloon for conveying the vascular stent. As shown in FIG. 3 and FIG. 4, the conveying balloon includes a balloon body 4 and a control pipeline 41 for filling the balloon body 4 with air or liquid. A light source 5 is disposed in the balloon body 4, and a side wall of the balloon body 4 is made of a light-transmitting material. In this way, by controlling the light emission of the light source 5, a flexible light-transmitting body 1 may be illuminated through the side wall of the balloon body 4, thereby completing the curing of a liquid photocuring supporting material 3.

In the present implementation, as shown in FIG. 4, the light source 5 includes a light beam 6 located in the balloon body 4. Multiple light-emitting diodes LED 7 are arranged on an outer wall of the light beam 6, wherein power lines of the multiple light-emitting diodes LED 7 may extend inside the light beam 6 and in a control pipeline, so as to realize control over the light source at an external end. In addition, in other possible implementations, a micro-battery and a wireless receiver may be received in the light column 6 as long as the size permits. In order to make full use of space, the light source 5 may be opened and closed by a remote controller in vitro, and may also be operated in a wired manner. In this case, a corresponding line may be received in the control pipeline 41 of the balloon. The control pipeline 41 may be used to convey air or liquid to achieve balloon expansion. In the present implementation, the balloon is a carbon dioxide inflatable balloon.

In an implanting system for a vascular stent provided in the present invention, the implanting system includes a stent conveying device for releasably receiving a vascular stent. The stent conveying device is any conveying device capable of conveying a flexible light-transmitting body 1 not filled with a liquid photocuring supporting material 3 to a designated position, such as a conveying balloon. In addition, in order to complete conveying of the liquid photocuring supporting material 3 after stent positioning, the implanting system further includes a light source 5 for illuminating the vascular stent, and a liquid supply pipe 8 for conveying the liquid photocuring supporting material 3. The liquid supply pipe 8 is detachably connected to the vascular stent. Thus, conveying, expansion and curing of the vascular stent are completed. There are two liquid supply pipes 8, preferably. One of the liquid supply pipes is used for liquid intake, and the other liquid supply pipe is used for air outlet, so as to smoothly complete the filling process of the liquid photocuring supporting material 3. In other implementations, the liquid supply pipes 8 may also be of other quantities as long as the filling of the liquid photocuring supporting material 3 can be completed. In addition, the light source 5 may enter the designated position for illuminating the vessel stent in various manners. In a preferred implementation of the present invention, the conveying device and the light source are of an integrated structure, that is, the conveying device is the above-mentioned conveying balloon provided in the present invention.

The light source 5 is arranged in the balloon body, which simplifies the structure and facilitates operation to increase efficiency.

Figure 5:
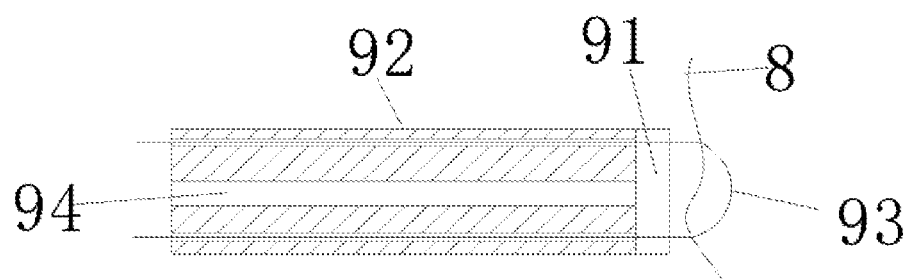
FIG. 5 is a sectional structure schematic diagram of a pipe cutting assembly provided by an implementation of the present invention, where a liquid supply pipe passes through a cutting wire.
Figure 6:
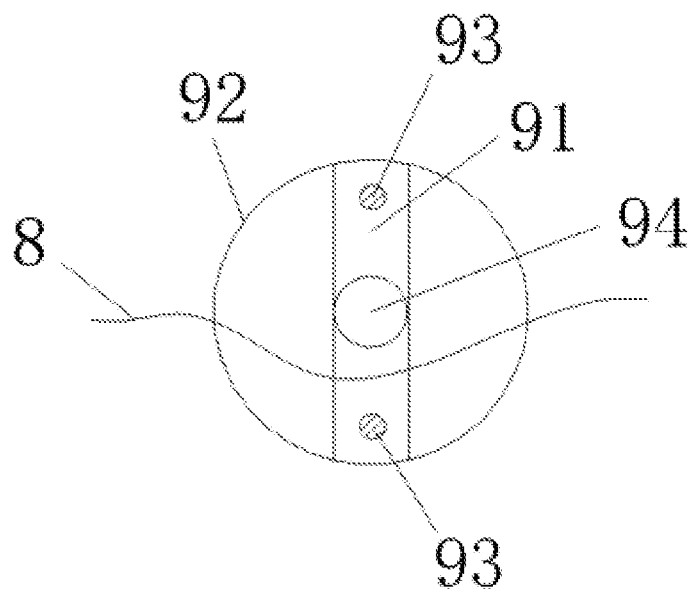
FIG. 6 is an end schematic diagram of a pipe cutting assembly provided by an implementation of the present invention, where a liquid supply pipe passes through a cutting wire, and the cutting wire is shown in section.

After the implantation of the vascular stent is completed, it is necessary to detach the liquid supply pipe 8 from the vascular stent, so as to realize the inward arrangement of the vascular stent. Specifically, in the present implementation, as shown in FIG. 5 and FIG. 6, the present implanting system further includes a pipe cutting assembly. The pipe cutting assembly includes a top core 92 and a cutting wire 93. A distal end surface of the top core is formed with a cutting groove 91. Two ends of the cutting wire movably penetrate through the top core 92 along the axial direction from the cutting groove 91 and stretch out from a proximal end, and the liquid supply pipe 8 passes between the cutting wire 93 and the cutting groove 91. In this way, a pipe cutting structure similar to a fodder chopper may be formed on the distal end surface of the top core 92. By controlling the two ends of the proximal end of the cutting wire 93, the cutting wire 93 may cut off the liquid supply pipe 8 between the cutting groove 91 and the cutting wire 93. The specific working process is as follows:

During the implantation process of the vascular stent, the liquid supply pipe 8 may be first passed through the cutting wire 93, and the top core 92 may be formed with a guide hole 94, which may be used for allowing a main body guide wire to pass during the implantation process of the vascular stent, so that the top core 92 may be controlled to move to a designated position with the implantation of the vessel stent. During the liquid supply process of the liquid supply pipe 8, the pipe cutting assembly does not work. When the liquid supply is finished, the cutting wire may be controlled to move toward the liquid supply pipe 8, and the liquid supply pipe 8 may be tightened first so that the liquid photocuring supporting material 3 does not exist at the tightening point. At this time, the illumination operation is performed until the liquid photocuring supporting material inside the vascular stent is fully cured, and then the liquid supply pipe 8 is further forcefully cut off on the end surface of the cutting groove through the cutting wire 93, thereby detaching the liquid supply pipe 8 from the vessel stent.

In other implementations, a one-way valve may also be provided on the vessel stent, and the liquid supply pipe 8 may be screwed into a liquid inlet of the one-way valve. In this way, since the one-way valve may prevent the liquid photocuring supporting material 3 from leaking out of the flexible light-transmitting body 1, the liquid supply pipe 8 may be detached from the vessel stent by screwing the liquid supply pipe 8 at the external end. Thus, the curing of the flexible light-transmitting body 1 is completed.

The preferred implementations of the present invention have been described in detail above with reference to the drawings. However, the present invention is not limited to specific details in the above implementations. Within the technical concept of the present invention, various simple variations of the technical schemes of the present invention can be performed. These simple variations all fall within the protection scope of the present invention.

In addition, it should be noted that the specific technical features described in the above specific implementations can be combined in any suitable manner without contradiction. To avoid unnecessary duplication, the present invention will not further describe various possible combination manners.

In addition, any combination of various different implementations of the present invention may also be performed as long as it does not violate the idea of the present invention, and it should also be regarded as the disclosure of the present invention.

What is claimed is:

1. An implanting system for implanting a vascular stent, comprising a vascular stent, a stent conveying device for releasably receiving the vascular stent, a light source for illuminating the vascular stent, and a liquid supply pipe for conveying a liquid photocuring supporting material, wherein the vascular stent comprises a flexible light-transmitting body, the flexible light-transmitting body being provided with a hardenable channel, the hardenable channel being arranged in a circumferential direction and an axial direction of the flexible light-transmitting body, wherein the hardenable channel is filled with a liquid photocuring supporting material, and the liquid photocuring supporting material is cured after being illuminated so as to radially support the flexible light-transmitting body; and the liquid supply pipe is detachably connected to the vascular stent, wherein the stent conveying device is a conveying balloon, the conveying balloon comprises a balloon body and a control pipeline for filling the balloon body with air or liquid, the light source is disposed in the balloon body, and a side wall of the balloon body is made of a light-transmitting material, the implanting system further comprising a pipe cutting assembly, the pipe cutting assembly comprising a top core and a cutting wire, a distal end surface of the top core being formed with a cutting groove, two ends of the cutting wire movably penetrating through the top core along the axial direction from the cutting groove and stretching out from a proximal end, and the liquid supply pipe passing between the cutting wire and the cutting groove.

2. The implanting system according to claim 1 wherein the liquid photocuring supporting material is UV resin.

3. The implanting system according to claim 1 wherein the hardenable channel is a spiral tubular structure extending along a side wall of the flexible light-transmitting body.

4. The implanting system according to claim 1, wherein the hardenable channel is a mesh structure arranged along a side wall of the flexible light-transmitting body.

5. The implanting system according to claim 1, wherein the vascular stent is an aortic vascular stent.

6. The implanting system according to claim 1, wherein the flexible light-transmitting body is made of a polyvinylidene fluoride material.

* * * * *